United States Patent

Ghyczy et al.

[11] Patent Number: 5,741,513
[45] Date of Patent: Apr. 21, 1998

[54] ALCOHOLIC AQUEOUS GEL-LIKE PHOSPHOLIPID COMPOSITION, ITS USE AND TOPICAL PREPARATIONS CONTAINING IT

[75] Inventors: Miklos Ghyczy, Köln; Joachim Roding, Wiesbaden; Hans Lautenschläger; Walter Hameister, both of Pulheim; Jörg Hager, Köln, all of Germany

[73] Assignee: A. Natterman & Cie. GmbH, Köln, Germany

[21] Appl. No.: 478,884

[22] Filed: Jun. 7, 1995

Related U.S. Application Data

[62] Division of Ser. No. 340,457, Nov. 14, 1994, abandoned, which is a continuation of Ser. No. 917,052, filed as PCT/EP91/00229, Feb. 6, 1991 published as WO91/11993, Aug. 22, 1991, abandoned.

[30] Foreign Application Priority Data

Feb. 8, 1990 [DE] Germany ............ 40 03 782.7
Feb. 8, 1990 [DE] Germany ............ 40 03 783.5

[51] Int. Cl.$^6$ ........................................ A61K 9/127
[52] U.S. Cl. ............ 424/450; 424/401; 264/4.1; 264/4.3; 514/944
[58] Field of Search ............ 424/450, 401; 264/4.1, 4.3; 514/944

[56] References Cited

U.S. PATENT DOCUMENTS 3,957,971 5/1976 Oleniacz .................. 424/70
4,954,345 9/1990 Muller .................... 424/450

FOREIGN PATENT DOCUMENTS 0051833 5/1982 European Pat. Off. .
0158441 10/1985 European Pat. Off. .

*Primary Examiner*—Gollamudi S. Kishore
*Attorney, Agent, or Firm*—Meltzer, Lippe, Goldstein, et al.

[57] ABSTRACT

An alcoholic, aqueous gel-like phospholipid composition is disclosed which contains, as alcohols, ethanol, 1-propanol or 2-propanol, which is characterized in that this composition is a liposomal gel composed of 15.00 to 30.00 parts by weight of a phospholipid concentrate, 14.00 to 20.00 parts by weight of alcohol and 50 to 71.00 parts by weight of an aqueous solution as the remainder. The use of this phospholipid composition for the preparation of liposomal solutions by dilution with a solution and topical preparations which contain these solutions are additionally disclosed.

8 Claims, 2 Drawing Sheets

ALCOHOLIC AQUEOUS GEL-LIKE PHOSPHOLIPID COMPOSITION, ITS USE AND TOPICAL PREPARATIONS CONTAINING IT

This application is a divisional of application Ser. No. 08/340,457, filed Nov. 14, 1994, now abandoned, which is a continuation of Ser. No. 07/917,052, filed as PCT/EP91/00229, Feb. 6, 1991 published as WO91/11993, Aug. 22, 1991, now abandoned, which is a national phase filing of International.

The present invention relates to an alcoholic, aqueous gel-like phospholipid composition and its use. The present invention furthermore relates to topical preparations containing it.

Gels are shape-retaining, easily deformable, liquid-rich disperse systems composed of at least two components. The best known and most widely distributed gels are the aqueous gels, in which water is used as the main component which is always present. Also known are the so-called organogels, in which the liquid main component is an organic solvent and an added apolar polymer which causes gelling and influences its strength.

Thus, WO 86/02264 describes a system of reversed micelles which can be converted into corresponding gels by addition of suitable solvents, such as, for example, squalene, Miglyol® or vegetable oils.

Systems were also investigated in which gels are formed from lecithin or general phospholipids, a solvent, water or other required auxiliaries. However, such gels are often only used as intermediates in order to form liposome dispersions from them as the desired final product.

Liposomes are spherical vesicles having a covering of one or more double layers (bilayer). They are preferably produced from lipids of natural origin. In the pharmaceutical industry and in the cosmetics sector, especially those liposomes composed of phospholipids play a crucial role. The most important phospholipid sources are soyabeans and other phospholipid-rich plants, for example rape or peanut, and to a lesser extent the phospholipids are also obtained from eggs or from animals.

Under certain conditions, phospholipids are able to form liposomes in aqueous solution (Bangham, A. D., Horne, R. W., J. Mol. Biol. 8 (1964), p. 660 et seq.). Since then, numerous attempts have been made to prepare stable liposomes which offer wide application possibilities. The method proposed by Bangham (Bangham, A. D., et al., Meth. in Membrane Biol. 1 (1976), pp. 1–68) of dissolving phospholipids in an organic solvent, removing the latter in a rotary evaporator to obtain, on the wall of the flask, a lipid film which then forms liposomes on dispersion in water or aqueous solution, cannot be carried out on the industrial scale. The liposomes prepared in this way can only be used for a small range of applications.

Liposomes can be converted into smaller, unilamellar vesicles by the sonication of multilamellar liposomes, as can be obtained, for example, by the above method, by means of ultrasound (C. Huang, Biochemistry 8 (1969), pp. 346–352).

Unilamellar liposomes can likewise be prepared at relatively low pressures by means of the "French press", which consists in forcing multilamellar liposome preparations prepared in a customary manner through a narrow opening (Hamilton, R. L., et al., J. Lipid Res. 21 (1980), pp. 981–992).

Another possibility for generating liposomal solutions is the ethanol injection method of Batzri and Korn (Batzri, S., Korn, E. D., Biochim. Biophys. Acta 298 (1976), pp. 1015–1019). In this method, the lipid dissolved in ethanol is injected into an aqueous buffer solution so that liposomes form. This process, exactly like the film method of Bangham, cannot be carried out on the industrial scale. In both methods, the organic—possibly even toxic—solvent additionally has to be removed in a complicated manner to obtain pharmaceutical or cosmetic preparations.

Large unilamellar liposomes are also formed when loaded lipids are suspended in a buffer in the presence of calcium cations (Papahadjopoulos, D., Ann. N.Y. Acad. Sci. 308 (1978) p. 751). After removal of the calcium cations, large unilamellar liposomes are then formed.

A recent method for the formation of liposomes consists in adding phospholipids in a cationic detergent to an organic solvent and transferring the lipid mixture to a finely divided or finely structured surface such as molecular sieve, quartz or zeolites (D. D. Lasic, J. of Coll. and Interface Sci. 124 82), (1988), pp. 428–435) and then removing the solvent in vacuo. In this way, phospholipid vesicles are formed directly.

The articles by Szoka, F. et al., in Ann. Rev. Biophys. Bioeng. 9 (1980), pp. 467–508 and Lasic, D. D. in Biochem. J. 256 (1988), pp. 1–11 give a general outline of the most commonly used methods for liposome preparation.

In EP-A-0 160 266 a liposome composition is claimed which consists of a three-dimensional network of liposomes and a network material. For the network material polysaccharides are preferably used in which the liposomes are embedded.

According to WO 85/03640, loaded liposomes in a gel matrix composed of starch or modified starch are claimed.

In EP-A-0 069 307 a method for the preparation of a liposome gel is described according to which an aqueous or solvent-containing lecithin solution is treated with ultrasound. Depending on the sonication period and sonication intensity, a more or less viscous gel is formed. By prolonging the sonication time or by means of mechanical stirring action, a liposome-containing aqueous solution is obtained as the final product.

A so-called preliposome gel is obtained from a mixture of phospholipids, fatty acids and a hydrating agent according to EP-A-0 211 647. Liposomes are formed after addition of water or buffer solution.

A phospholipid-containing, highly fluid gel is claimed in WO 89/00077 for use as aerosol liposomes. The system consists of lecithin, an organic solvent and a little water. A broad span of liposome diameters in the range from 100 to 2500 nm occurs here; a high solvent content must be selected for a worthwhile application range.

U.S. Pat. No. 2,090,537 relates to a process for the preparation of "water-containing" lecithin (lecithin hydrate), consisting of a homogeneous mixture of preferably 15–25% vegetable lecithin, preferably 8–25% alcohol, in particular ethanol or isopropanol, and 58–78% water as the remainder. The water-containing lecithin is obtained by heating water and alcohol preferably to about 71° C. (160° F.), adding the lecithin and stirring. After cooling to room temperature, a phase separation occurs in which the lowermost phase of the three phases contains the lecithin hydrate. This lecithin phase, saturated with alcohol, water and oil, is already adequately stable as such and can be further purified by removal of the alcohol or a part of the water in vacuo, the water-containing lecithin being obtained. Alternatively, this phase can be obtained as a gel by acidifying to pH 4 to pH 6.

EP-A-0 158 441 relates to a liquid composition containing a homogeneous mixture of at least one membrane lipid, at least one water-miscible organic solvent, for example ethanol or propylene glycol which serves as a solvent for the lipid, and optionally an amount of water, which is characterized in that this composition spontaneously forms vesicles or liposomes on addition of more water, the weight ratio of lipid:solvent being 40:1 to 1:20.

EP-A-0 240 346 describes a preparation process for liposomes having an enlarged reservoir for active substances using the following process steps:

1. preparation of a liposome with and without an active-substance reservoir from a phospholipid;
2. dispersion of the liposome in an active substance-containing liquid;
3. addition of a slightly volatile organic solvent to the dispersion with gel formation; and then
4. removal of this organic solvent by evaporation and reconstitution of the liposomes.

The liposomes according to process step 1 are either obtained as multilamellar liposomes in a manner known per se or as unilamellar liposomes by ultrasonic treatment. The liposomes according to process step 4 no longer contain substantial amounts of organic solvents after their working-up.

The present application is based on the object of providing an alcoholic, aqueous gel-like phospholipid composition which is self-preserving, storable and transparent.

This object is achieved by the gel-like phospholipid composition being a liposomal gel, i.e. a system built up exclusively from liposomes, which consists of a phospholipid concentrate of specific composition, alcohol and water in specific concentrations and whose aqueous phase is virtually exclusively the internal phase.

The invention thus relates to an alcoholic, aqueous gel-like phospholipid composition which, as alcohol, contains ethanol, 1-propanol, 2-propanol or mixtures thereof, which is characterized in that the phospholipid composition is a liposomal gel of the following composition:

| | |
|---|---|
| 15.00–30.00 | parts by weight of a phospholipid concentrate, consisting of |
| 70.00–80.00 | parts by weight of phosphatidylcholine, |
| 15.00–5.00 | parts by weight of acidic phospholipids, |
| 5.00–25.00 | parts by weight of other phospholipids, |

The gel-like phospholipid composition according to the invention has a transparent structure which is homogeneous and substantially free of agglomerates and other clouding agents and has a mean particle size of 200 nm±20%. (Electron microscopy, freeze-fracture). The liposomal solution obtained from the gel-like phospholipid composition by dilution with aqueous solution preferably has an average liposome size of 200 nm±20% (determined by the laser light-scattering method) and is thus preferably employed in topical preparations, such as cosmetic or pharmaceutical preparations, which require a liposome particle diameter of 100–400 nm, preferably 100–200 nm. A particular advantage is that these liposomes remain transparent, in dependence of active substance, not only in the unloaded state, but also in the loaded state. Additionally, both the gel and the liposomal solution can be prepared in sterile and pyrogen-free form, according to German Pharmacopeia 9, so that they can be formulated to give cosmetic and pharmaceutical preparations without additional, possibly allergenic, preservatives. Furthermore, it has been surprising for the person skilled in the art that alcohol in concentrations of 14 to 20% by weight does not lead to destruction of the liposome solution.

Finally, a liposomal solution can be obtained in an industrially simple manner from the phospholipid composition (liposome gel) according to the invention without having to carry out process steps which are industrially and energetically complex, that is to say in particular without increasing the temperature or employing ultrasound.

The phospholipid concentrates, as one of the constituents of the phospholipid composition according to the invention, are obtained from natural phospholipid mixtures, for example from oil seeds, such as soybean, rape, sunflower etc.

An enrichment process for the preparation of phospholipid concentrates of this type is described in EP-A-0 069 770. Phospholipid concentrates of this type consist of phospholipids (phosphatidylcholine, acidic phospholipids and other phospholipids) and phosphorus-free associated lipids. The acidic phospholipids include phosphatidylethanolamine, phosphatidic acid and also N-acylphosphatidylethanolamine. The other phospholipids include lysophosphatidylcholine and phosphatidylinositol. The phosphorus-free associated lipids include, inter alia, glycolipids and phytolipids. The phosphorus-free associated lipids are present in the phospholipid concentrates in 1–15 parts by weight, preferably 1–9 parts by weight, particularly preferably 1–5 parts by weight, relative to 100 parts by weight of phospholipids.

The phospholipid concentrate described above thus has the following composition:

| | |
|---|---|
| 60.87–79.21% | by weight of phosphatidylcholine |
| 14.85–4.35% | by weight of acidic phospholipids |
| 4.95–21.74% | by weight of other phospholipids and |
| 0.99–13.04% | by weight of phosphorus-free associated lipids. |

A further preferred embodiment of the phospholipid concentrate as a constituent of the phospholipid composition according to the invention is a mixture of 80 parts by weight of phosphatidylcholine, 5–15 parts by weight of acidic phospholipids, and 15–5 parts by weight of other phospholipids, this concentrate furthermore containing 1–9 parts by weight of phosphorus-free associated lipids per 100 parts by weight of the above phospholipids. A preferred phospholipid concentrate of this type thus has the following composition:

| | |
|---|---|
| 73.39–79.21% | by weight of phosphatidylcholine, |
| 4.95–13.76% | by weight of acidic phospholipids, |
| 14.85–4.59% | by weight of other phospholipids and |
| 0.99–8.26% | by weight of phosphorus-free associated lipids. |

The phospholipid concentrate is employed in amounts from 15.00 to 30.00 parts by weight, preferably 20.20 to 30.00 parts by weight/100 parts by weight of the phospholipid composition according to the invention.

The alcohol is employed in amounts of 14 to 20 parts by weight, preferably about 16 parts by weight, per 100 parts by weight of the phospholipid composition according to the invention.

The aqueous solution is employed in amounts of 50 to 71.00 parts by weight, preferably 54.00 to 63.80 parts by weight, per 100 parts by weight of the phospholipid composition. Aqueous solution in the sense of the present invention is understood as meaning once-distilled water, tap water, purified water, German Pharmacopeia 9, demineralized water, and also buffer solutions, such as, for example, phosphate buffer or a physiological saline solution.

In the liposomal solution obtained by dilution of the phospholipid composition with stirring, the constituents are present in the following concentrations:

The phospholipid concentrate is present in the liposomal solution in amounts from 10.10 to 20.20 parts by weight, preferably 10.10 parts by weight, relative to 100 parts by weight of the total liposomal solution. The alcohol is present in the liposomal solution in amounts from about 16 parts by weight, relative to 100 parts by weight of the total liposomal solution. The aqueous solution is present in the liposomal solution in amounts from 63.80 to 73.90 parts by weight, relative to 100 parts by weight of the total liposomal solution. According to a preferred embodiment of the present invention, at least one biologically active substance can be admixed to the liposomal gel. Examples of active substances of this type are anti-inflammatories such as ketoprofen, bisabolol etc., anticoagulants such as heparin, hirudin etc., antimycotics, and also spasmolytics or circulation-promoting agents such as papaverine.

The present invention furthermore relates to topical preparations which contain at least one of the phospholipid compositions described above in combination with at least one biologically active substance and customary auxiliaries and additives. Biologically active substances which are intended to be administered in combination with gels are, for example, the active substances described above.

The present invention furthermore relates to pharmaceutical preparations which contain at least one phospholipid composition of the type described above in combination with at least one biologically active substance, preferably for the treatment of the indications described above.

The present invention finally relates to cosmetic preparations which contain at least one phospholipid composition described above in combination with at least one cosmetic active substance for care of the skin and hair, it preferably being a caring agent penetrating into the horny skin, such as, for example, urea, elastin etc.

A particularly preferred embodiment of the present invention is a gel which consists of 20% phospholipid (having a content of 80% phosphatidylcholine) and 16% ethanol and which is specified by the following parameters:

| Appearance | golden brown slightly cloudy gel |
|---|---|
| Transmission (c = 0.5% in water, 660 nm) | at least 50% (German Pharmacopeia 9, vol. 6.19) |
| Viscosity (measured at 20° C.) | 5000 ± 2000 mPa · s |

Electron microscopical investigation by the method of M üller, T. et al., Seifen Öle Fette Wachse 3, 88–89 (1989) shows, after use of the freeze-fracture technique, the liposomal structure of the gel (FIG. 1).

The liposomes were detected by the method described by Zellmann et al., ZEISS Application EM 902 Cryo, 1989 (FIG. 2).

The present invention is illustrated in greater detail below by means of 2 figures which show preferred embodiments of the invention.

Figure 1:
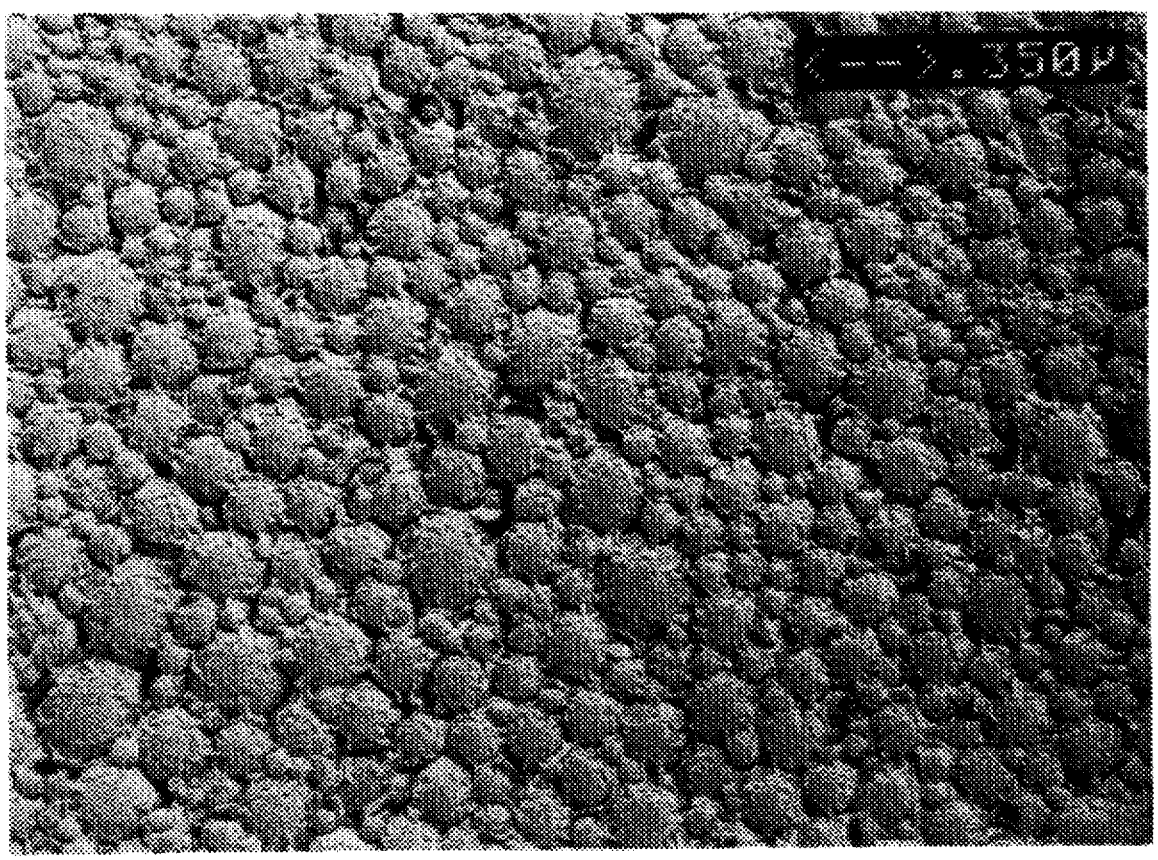
FIG. 1: The liposomes of the sample, prepared by the freeze-fracture technique, of the gel prepared according to the invention are shown in the form of an electron micrograph. The liposomes form a vesicular gel. They are in close contact with one another and additional water cannot be seen. (1 measuring unit corresponds to 350 nm).
Figure 2:
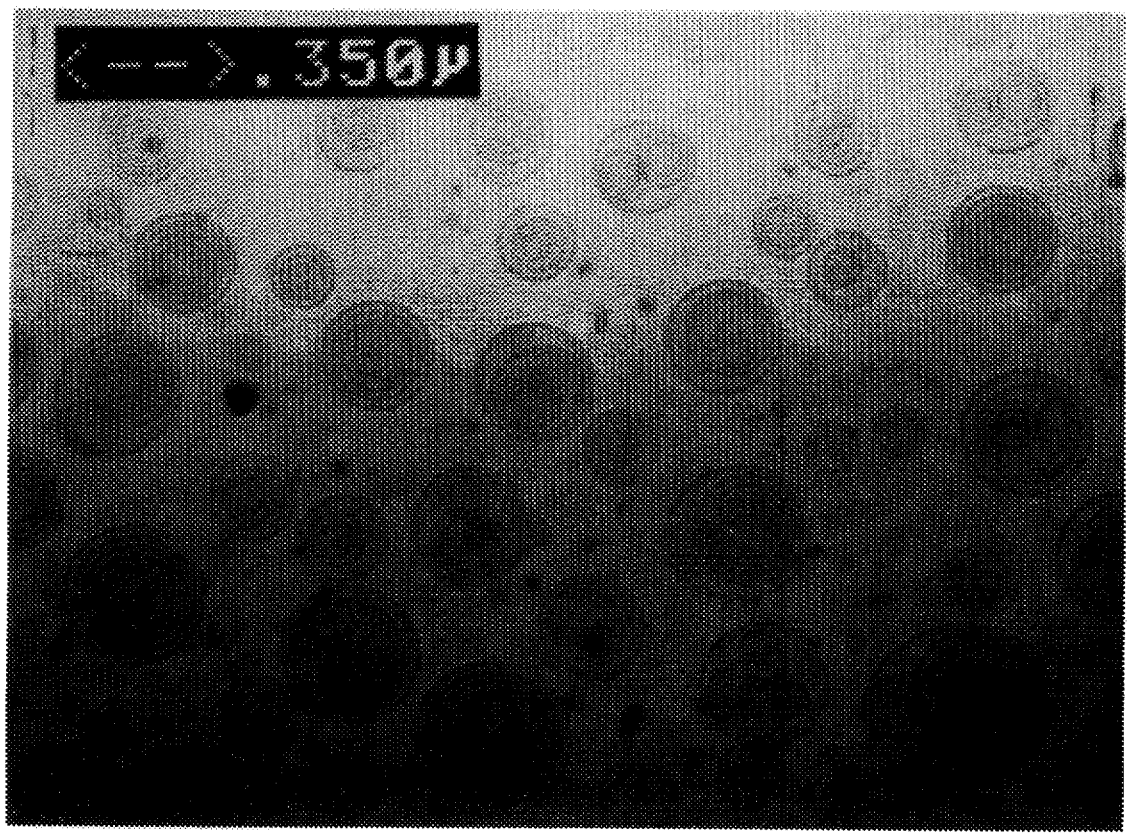
FIG. 2: The cryoelectron micrograph of a 3% strength dispersion of the gel prepared according to the invention in water shows that such a preparation exclusively contains multilamellar liposomes. (1 measuring unit corresponds to 350 nm). The gel-like phospholipid composition is prepared in an industrially particularly simple manner by stirring the phospholipid concentrate of determined composition with a determined amount of alcohol for a short time and inducing gel formation by addition of water and further stirring. The stirring can be carried out using any commercially available stirrer.

However, this stirrer must have a sufficiently high speed so that thorough mixing is achieved in a short time. In this process, the starting material is a phospholipid composition which in general has a pH in the range from 5 to 8, preferably 6.5 to 7.5.

The invention will now be illustrated in greater detail by exemplary embodiments, the following phospholipid concentrate composition being used:

The phospholipid contents of this composition consist of:

phosphatidylcholine 80%;

acidic phospholipids 15%;

other phopholipids 5%

The content of the phosphorous-free associated lipids is 5 parts by weight, relative to 100 parts by weight of phospholipids, i.e. 4.76% by weight of phosphorus-free associated lipids are present.

EXAMPLE 1

10.48 g of the phospholipid concentrate (containing 10 g of phospholipids) are dissolved in 8 g of ethanol with stirring. The solution has a viscosity of 806 mPa.s (at 25° C.) and is homogeneous. The solution is homogenized for 3 min. with 31.52 g of demineralized water, a commercially available high-speed laboratory stirrer being used. A transparent gel containing 20.96% by weight of phospholipid concentrate (20% by weight of phospholipids) is obtained.

EXAMPLE 2

15.72 g of the phospholipid concentrate (containing 15 g of phospholipids) are dissolved in 8 g of ethanol analogously to Example 1. The solution is stirred for 3 min. with 26.28 g of demineralized water until a homogeneous, transparent gel is formed. The gel contains 31.4% by weight of phospholipid concentrate (30% by weight of phospholipids).

EXAMPLE 3

15.72 g of the phospholipid concentrate (containing 15 g of phospholipids) are dissolved in 8 g of 2-propanol analogously to Example 1. 26.28 g of demineralized water are added and the mixture is stirred for a further 3 min. A transparent gel is formed which contains 31.40% by weight of phospholipid concentrate (30.00 parts by weight of phospholipids).

EXAMPLE 4

10.48 g of the phospholipid concentrate (containing 10 g of phospholipids) are dissolved in 8 g of 2-propanol as in Example 1. After addition of 36.52 g of demineralized water, the mixture is stirred for 3 min. and a transparent gel is obtained containing 19.05% by weight of phospholipid concentrate (18.18% by weight of phospholipids).

The following examples show how liposomal solutions are obtained from the phospholipid-containing liposomal gel by means of simple process steps.

EXAMPLE 5

The entire amount of the phospholipid gel (50 g) obtained in Example 1 is mixed with 42 g of 0.2 molar phosphate buffer solution of pH 7.4 and stirred for 4 min. The resulting highly fluid dispersion is mixed with 8 g of ethanol and additionally stirred for a further minute to give the ready-to-use final product. The proportions of phospholipid concentrate:ethanol:aqueous solution are 20.96:16:73.04 (phospholipid:ethanol:water are 10:16:74). The mean particle size, measured by the laser light-scattering method, is 204 nm (±20%).

EXAMPLE 6

The entire amount of the phospholipid gel (50 g) obtained in Example 2 is mixed with 84 g of tap water, stirred for 4 min. and 16 g of ethanol are then added. After a further stirring time of 1 min., a liposomal solution having an ethanol content of 16% by weight and 10.48% by weight of phospholipid concentrate (corresponding to 10% by weight of phospholipids) and a mean particle size of 194 nm (±20%) is obtained as the final product. In spite of the use of tap water, which is usually contaminated with microorganisms and salts, the product contains less than 100 microorganisms per gram.

EXAMPLE 7

111 g of physiological saline solution (0.9% by weight sodium chloride) are added to the entire amount of gel from Example 4 analogously to Example 6. After stirring for 4 min., a further 24 g of 2-propanol are added and the mixture is stirred for a further minute. The mean particle size of the vesicles in the liposomal solution is 200 nm (±20%).

EXAMPLE 8

The phospholipid gel obtained in Example 4 is mixed with stirring with 37 g of 0.2 molar phosphate buffer solution, stirred for 4 min., 8 g of 2-propanol are added and the mixture is additionally stirred for a further 1 min. The mean particle size of the vesicles in the liposomal solution is 187 nm (±20%).

The number of microorganisms in the gel-like phospholipid compositions according to the invention according to Examples 1 to 4 and the liposomal solutions obtained from these according to the invention according to Examples 5 to 8 was determined in accordance with the requirements of German Pharmacopeia 9 for Medicaments of category 2, Preparations for topical or other types of local application. In all cases, the number of microorganisms was below 100 microorganisms/g of the preparation and thus corresponds to the requirements of German Pharmacopeia 9.

Preparations containing biologically active substances

The liposomes which are present in the gel prepared according to the invention (FIG. 1) can be loaded with various active substances. Surprisingly, loading can be carried out both with lipophilic (for example bisabolol) and with hydrophilic (for example papaverine×HCl) substances.
Preparation 1

97.0 g of gel prepared according to the invention as in Example 1 are stirred with 3.0 g of bisabolol at 50° C. for 10 min by means of a propeller stirrer. 15.0 g of this mixture are diluted with 85.00 g of demineralized water. The mean particle size of a solution diluted to 0.01% phospholipid with demineralized water was 215 nm (laser light-scattering).
Preparation 2

4.0 g of papaverine *HCl are dissolved in 36.0 g of ethanol and homogenized with 360.0 g of gel prepared according to the invention as in Example 1 in a rapidly stirring mixer. The mean particle size was 175 nm (laser light-scattering).
Preparation 3

1.43 g of hirudin (100,000 ATU/100 g) are stirred with 98.57 g of the gel prepared according to the invention as in Example 1 in a Fanta bowl and homogenized in a rapidly stirring mixer. The mean particle size was 151 nm (laser light-scattering) and the pH was 6.9.
Preparation 4

1.98 g of heparin Na are dissolved in 40.0 g of ethanol, 204.33 g of demineralized water and 3.7 g of NaCl by means of a magnetic stirrer. This solution is homogenized with 250.0 g of gel prepared according to the invention as in Example 1 using a rapidly stirring mixer. The mean particle size of a solution diluted to 0.01% phospholipid with demineralized water was 231 nm and the pH was 6.5.
Preparation 5

1.0 g of ketoprofen are stirred in a Fanta bowl with 1.60 g of ethanol, 90.0 g of gel prepared according to the invention as in Example 1, 8.4 g of demineralized water and 0.60 g of 10% strength aqueous sodium hydroxide solution. The mean particle size of a solution diluted to 0.01% phospholipid with demineralized water was 216 nm.
Preparation 6

5 g of urea are stirred with 20 g of the gel prepared as in Example 1 and then diluted to 3% phospholipid with demineralized water. Liposomes having a mean particle size of 175 nm are formed.
Preparation 7

5 g of elastin are stirred with 20 g of the gel prepared as in Example 1 and then diluted to 3% phospholipid with demineralized water. Liposomes having a mean particle size of 171 nm are formed.

We claim:

1. A method for preparing a liposomal solution comprising:
   (a) dissolving in at least one alcohol a phospholipid concentrate comprising
       (i) 70–80 parts by weight of phosphatidylcholine,
       (ii) 15–5 parts by weight of at least one phospholipid selected from the group consisting of phosphatidylethanolamine, phosphatidic acid, N-acylphosphatidylethanolamine, and mixtures thereof,
       (iii) 5–25 parts by weight of at least one other phospholipid selected from the group consisting of lysophosphatidylcholine, phosphatidylinositol and mixtures thereof, and
       (iv) 1–15 parts by weight of at least one phosphorus-free lipid per 100 parts by weight of (i), (ii) and (iii);
   (b) adding an aqueous solution to produce a liposomal gel comprising
       (i) 15–30 parts by weight of said phospholipid concentrate,
       (ii) 20–14 parts by weight of said one alcohol, and
       (iii) 50–71 parts by weight of said aqueous solution, and
   (c) adding a further amount of water to convert said liposomal gel to said liposomal solution.

2. A method for preparing a liposomal solution comprising
   (a) dissolving in about 16 parts by weight of at least one alcohol a phospholipid concentrate comprising
      (i) 70–80 parts by weight of phosphatidylcholine,
      (ii) 15–5 parts by weight of at least one phospholipid selected from the group consisting of phosphatidylethanolamine, phosphatidic acid, N-acylphosphatidylethanolamine, and mixtures thereof;
      (iii) 5–25 parts by weight of at least one phospholipid selected from the group consisting of lysophosphatidylcholine, phosphatidylinositol and mixtures thereof, and
      (iv) 1–15 parts by weight of at least one phosphorus-free lipid per 100 parts by weight of (i), (ii), and (iii);
   (b) adding an aqueous solution to produce a liposomal gel comprising
      (i) 15–30 parts by weight of phospholipid concentrate
      (ii) about 16 parts by weight of said alcohol, and
      (iii) 50–71 parts by weight of said aqueous solution, and
   (e) adding a further amount of water to convert to said liposomal gel to said liposomal solution.

3. The method according to claim 1 wherein the water-containing solution comprises at least one biologically active substance selected from the group consisting of anti-inflammatories, anti-coagulants, antimycotics, spasmolytics and vasodilators.

4. The method according to claim 2 wherein the water-containing solution comprises at least one biologically active substance selected from the group consisting of anti-inflammatories, anti-coagulants, antimycotics, spasmolytics and vasodilators.

5. The method according to claim 1 wherein the water-containing solution comprises at least one cosmetic skin-care agent.

6. The method according to claim 2 wherein the water-containing solution comprises at least one cosmetic skin-care agent.

7. The method according to claim 5 wherein the cosmetic skin-care agent is selected from the group consisting of urea and elastin.

8. The method according to claim 6 wherein the cosmetic skin-care agent is selected from the group consisting of urea and elastin.

* * * * *